United States Patent
Milczynski et al.

(10) Patent No.: US 9,511,225 B2
(45) Date of Patent: Dec. 6, 2016

(54) HEARING SYSTEM COMPRISING AN AUDITORY PROSTHESIS DEVICE AND A HEARING AID

(71) Applicant: ADVANCED BIONICS AG, Staefa (CH)

(72) Inventors: Matthias Milczynski, Valencia, CA (US); Stefan Fredelake, Hannover (DE)

(73) Assignee: Advanced Bionics AG, Staefa (CH)

(*) Notice: Subject to any disclaimer, the term of this patent is extended or adjusted under 35 U.S.C. 154(b) by 0 days.

(21) Appl. No.: 14/763,148

(22) PCT Filed: Jan. 24, 2013

(86) PCT No.: PCT/EP2013/051338
§ 371 (c)(1),
(2) Date: Jul. 23, 2015

(87) PCT Pub. No.: WO2014/114337
PCT Pub. Date: Jul. 31, 2014

(65) Prior Publication Data
US 2015/0367132 A1  Dec. 24, 2015

(51) Int. Cl.
*A61N 1/00* (2006.01)
*A61N 1/36* (2006.01)
(Continued)

(52) U.S. Cl.
CPC ......... *A61N 1/36032* (2013.01); *A61N 1/0541* (2013.01); *H04R 25/606* (2013.01)

(58) Field of Classification Search
CPC .. A61N 1/36032; A61N 1/0541; H04R 25/50; H04R 25/48; H04R 25/353; H04R 25/43
See application file for complete search history.

(56) References Cited

U.S. PATENT DOCUMENTS

| | | |
|---|---|---|
| 6,694,291 B2 | 2/2004 | Mauro et al. |
| 8,280,087 B1 | 10/2012 | Bacon et al. |

(Continued)

FOREIGN PATENT DOCUMENTS

| | | |
|---|---|---|
| DE | 10200806005 | 8/2010 |
| EP | 2375782 | 10/2011 |

(Continued)

OTHER PUBLICATIONS

International Search Report and Written Opinion received in International Application No. PCT/EP2013/051338, dated Oct. 7, 2013.
(Continued)

*Primary Examiner* — Robert N Wieland
(74) *Attorney, Agent, or Firm* — ALG Intellectual Property, LLC

(57) ABSTRACT

There is provided a hearing assistance system comprising an auditory prosthesis device for neural stimulation of a patient's hearing at one of the patient's ears and a hearing aid for acoustic stimulation of the patient's hearing at the same one or the other one of the patient's ears. The system includes at least one microphone for capturing an input audio signal from ambient sound; and a fundamental frequency estimation unit for estimating the fundamental frequency and at least part of its harmonics at least for voiced segments of the input audio signal and for supplying a corresponding output signal.

26 Claims, 4 Drawing Sheets

(51) Int. Cl.
*A61N 1/05* (2006.01)
*H04R 25/00* (2006.01)

(56) References Cited

U.S. PATENT DOCUMENTS

| | | |
|---|---|---|
| 2007/0135862 A1 | 6/2007 | Nicolai et al. |
| 2007/0189561 A1 | 8/2007 | Dijkstra et al. |
| 2011/0142271 A1 | 6/2011 | Tiefenau |
| 2011/0238176 A1 | 9/2011 | Bradley et al. |
| 2015/0126802 A1* | 5/2015 | Lim .................. A61H 23/0236 600/13 |

FOREIGN PATENT DOCUMENTS

| | | |
|---|---|---|
| WO | WO-92/08330 | 5/1992 |
| WO | WO-2010/088722 | 8/2010 |
| WO | WO-2011/032021 | 3/2011 |

OTHER PUBLICATIONS

Milczynski, et al., "Improved fundamental frequency coding in cochlear implant signal processing", *The Journal of the Acoustical Society of America, American Institute of Physics for the Acoustical Society of America*, New York, NY, vol. 125, No. 4, Apr. 30, 2009.

Vandali, et al., "Development of a temporal fundamental frequency coding strategy for cochlear implants", *J. Acoust. Soc. Am.* 1929(6), 2011, pp. 4023 to 4036.

Laneau, et al., "Improved music perception with explicit pitch coding in cochlear implants", *Audiology & Neurotology* 2006(11), pp. 38 to 52.

Green, et al., "Enhancement of temporal periodicity cues in cochlear implants, effects on prosodic perception and vowel identification", *J. Acoust. Soc. Am*.118(1), pp. 375 to 385.

Green, et al., "Enhancing temporal cues to voice pitch in continuous interleaved sampling cochlear implants", *J. Acoust. Soc. Am.* 116(4), 2004, pp. 2298 to 2310.

* cited by examiner

HEARING SYSTEM COMPRISING AN AUDITORY PROSTHESIS DEVICE AND A HEARING AID

The invention relates to a hearing system comprising an auditory prosthesis device for neural stimulation of a patient's hearing at one of the patient's ears and a hearing aid for acoustic stimulation of the patient's hearing at the same ear or at the other ear.

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to excite the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from severe to profound sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and N-of-M stimulation (wherein stimulation current is only applied to N of M total stimulation channels during a particular stimulation frame).

An example for such a CI device with electrical cochlea stimulation is described in WO 2011/032021 A1.

Patients who are precluded from the use of a cochlear implant due to illness or injury damaging the cochlea or auditory nerve, may be provided with an auditory brainstem implant or an auditory midbrain implant. Such devices use similar technology as a cochlear implant, but instead of electrical stimulation being used to stimulate the cochlea, it is used to stimulate the brainstem or midbrain of the recipient.

Nowadays, combinations of devices using different types of stimulation on one ear or on different ears are possible. For example, electro-acoustic stimulation (EAS) makes use of a CI electrode for electric stimulation in the range of the higher frequencies and a hearing aid for acoustic stimulation in the range of the lower frequencies in the same ear. On the other hand, bimodal systems use a configuration with a CI device on one ear and a hearing aid on the other ear. Increased speech intelligibility performance was found when the hearing aid was additionally switched onto the electric stimulation. One possible reason for this benefit is the transmission of the pitch in low acoustic frequencies.

However, for classic CI devices the pitch is transmitted only insufficiently, resulting in severe problems in music listening and speaker segregation based on pitch differences.

An example of a bimodal system is found in US 2011/0238176 A1, wherein electric stimuli are provided only to that parts of the cochlea that have reduced or no residual hearing, with also timing differences between acoustic and electric stimuli being corrected for. A further example of a bimodal system is described in DE 10 2008 060 056 A1.

There are several approaches for CI coding strategies aiming at improving the pitch perception by means of enhancing the temporal information delivered to spectral channels. For example, US 2006/080087 A1 relates to a CI system using enhanced modulation depth in the temporal envelope of each CI channel stimulation signal, including phase alignment of modulated signals across the channels; the system also includes voice detection capability.

WO 2010/088722 A1 relates to a CI system using a coding strategy in which an additional fundamental frequency estimator is employed, with an additional harmonic probability estimator determining the amount of enhanced fundamental frequency information delivered to each spectral channel. A similar approach is described in "Development of a temporal fundamental frequency coding strategy for cochlear implants", by A. Vandali et al., J. Acoust. Soc. Am. 1929(6), 2011, pages 4023 to 4036.

In the article "Improved fundamental frequency coding in cochlear implant signal processing" by M. Milczynski et al., J. Acoust. Soc. Am. 125(4), 2009, pages 2260 to 2271, a CI coding strategy is described which applies a sinusoidal modulator using the fundamental frequency as the modulation frequency to each spectral channel at full modulation depth and in phase across channels, with this strategy being applied only for voiced speech segments. The processing strategy employs a fundamental frequency estimator and a voiced/unvoiced detector. Similar approaches are described in the articles "Improved music perception with explicit pitch coding in cochlear implants" by J. Laneau et al., in Audiology & Neurotology 2006(11), pages 38 to 52; "Enhancement of temporal periodicity cues in cochlear implants, effects on prosodic perception and vowel identification", by T. Green et al., J. Acoust. Soc. Am. 118(1), pages 375 to 385; and "Enhancing temporal cues to voice pitch in continuous interleaved sampling cochlear implants", by T. Green et al., J. Acoust. Soc. Am. 116(4), 2004, pages 2298 to 2310.

U.S. Pat. No. 6,694,291 B2 relates to a mobile phone comprising a voice detector and a fundamental frequency estimator, wherein the spectral content of low frequencies determined by the fundamental frequency estimator is enhanced and a noise suppression system is used to determine the signal-to-noise ratio in each frequency band.

It is an object of the invention to provide for a hearing system providing for enhanced pitch perception.

According to the invention, this object is achieved by a hearing system as defined in claim 1 and a method as defined in claim 26.

The invention is beneficial in that, by combining an auditory prosthesis device for neural stimulation and a hearing aid for acoustic stimulation and by providing the auditory prosthesis device with an electric signal pitch enhancement unit supplied with the output signal of a fundamental frequency estimation unit for applying a modified pitch processing to at least part of the input audio signals and simultaneously providing the hearing aid with an acoustic signal pitch enhancement unit also supplied with the output signal of the fundamental frequency estimation unit for applying a modified pitch processing to at least part of the input audio signals, an optimized pitch processing can be achieved which results in enhanced pitch perception by the patient.

Preferred embodiments of the invention are defined in the dependent claims.

Hereinafter, examples of the invention will be illustrated by reference to the attached drawings, wherein.

Figure 6:
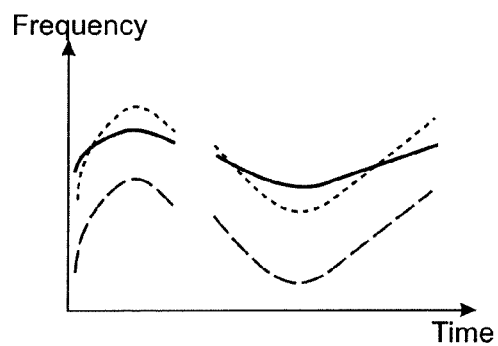
Figure 7:
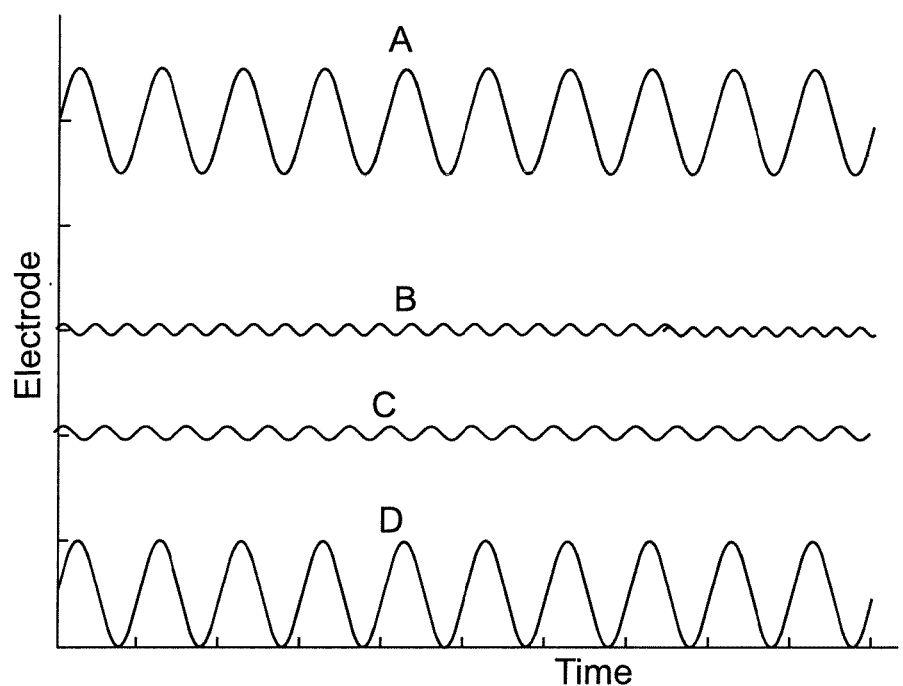

FIG. 6 illustrates an example of pitch enhancement by enhancement of the frequency modulation index (dotted line versus solid line of the original signal) and shifting of the fundamental frequency into an audible range (dashed line versus dotted line), with the fundamental frequency of the signal in the acoustic domain being shown as a function of time; and FIG. 7 illustrates an example of the stimulation current versus time for several CI electrodes.

Figure 1:
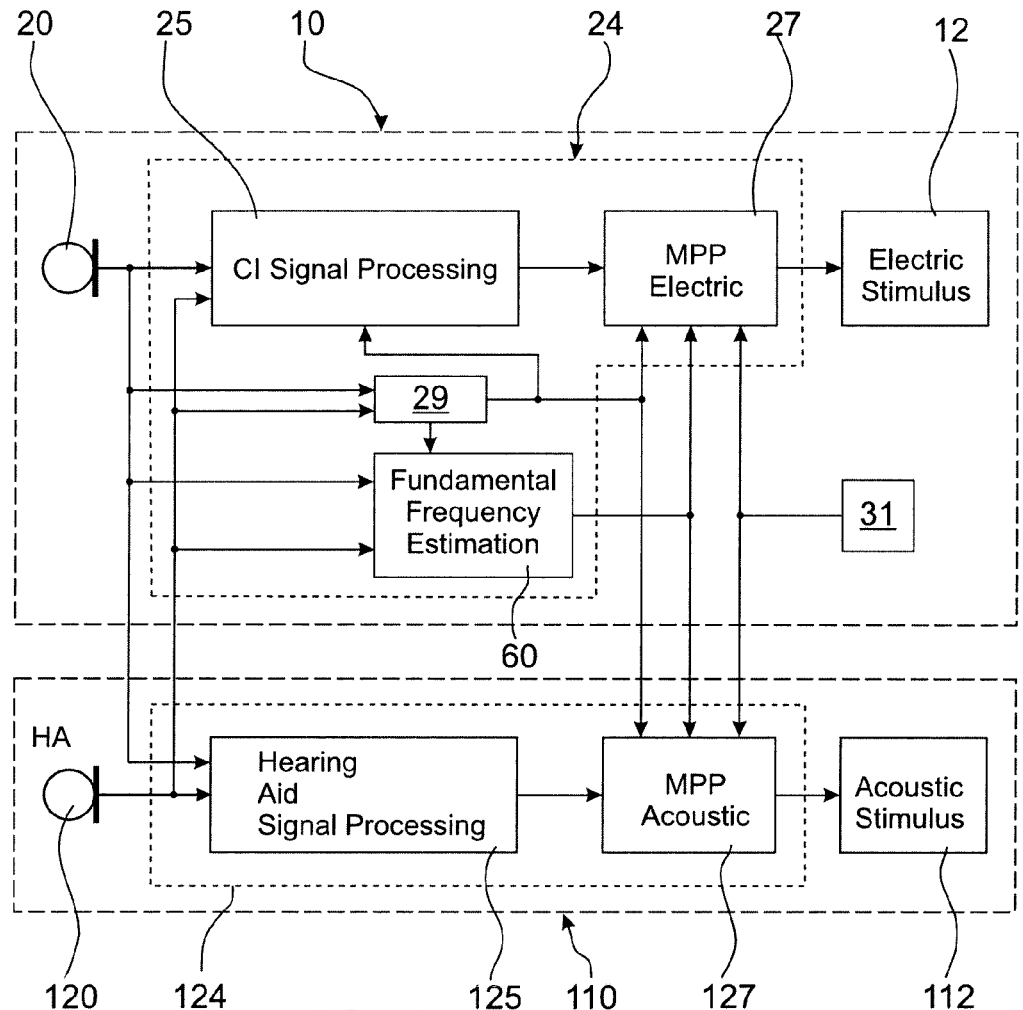
FIG. 1 is a schematic block diagram of an example of a hearing system according to the invention.

FIG. 1 is a schematic block diagram of an example of a hearing system according to the invention, comprising an auditory prosthesis device (which, in the example of FIG. 1 is a CI device 10) and a hearing aid 110 which, according to one embodiment, may be worn at the same ear, thereby forming an EAS system, or, according to an alternative embodiment, may be worn at different ears, thereby forming a bimodal system. In particular, an EAS system may combine the functionality of a CI device and a hearing aid within a single integral device (in case of such integral device "CI device" and "hearing aid" are to be understood as functional sub-systems or components of the integral EAS system, rather than as physically separated devices).

The CI device 10 comprises at least one microphone 20 for capturing an input audio signal from ambient sound, a sound processor 24 for generating a neural stimulation signal from at least part of the input audio signal, and an implantable stimulation assembly 12 for stimulation of the patients hearing according to the neural stimulation signal.

The hearing aid 110 comprises an audio signal processing unit 124 for processing at least a part of an input audio signal captured from ambient sound and an electro-acoustic output transducer (loudspeaker) 112 for stimulating the patients hearing according to the processed audio signals. In the example of FIG. 1, the hearing aid 110 comprises at least one microphone 120 for capturing an input audio signal from ambient sound.

While in the example of FIG. 1 both the CI device 10 and the hearing aid 110 are provided with their own microphone 20, 120, with the audio signal of each of the microphones 20, 120 being supplied both to the sound processor 24 of the CI device 10 and to the audio signal processing unit 124 of the hearing aid 110, the CI device 10 and the hearing aid 110 may share a common microphone in case that the CI device 10 and the hearing aid 110 are used at the same ear, in particular in case of an integral EAS device.

In the example of FIG. 1, the CI device 10 is provided with a fundamental frequency estimation unit 60 which is supplied with the audio signal of at least one of the microphones 20, 120 in order to estimate the fundamental frequency of the input audio signal. However, according to an alternative embodiment, the fundamental frequency estimation unit 60 may be provided as part of the hearing aid 110.

The sound processor 24 comprises a signal processing block 25 for processing of the input audio signal and an electric signal pitch enhancement unit 27 which is supplied with the output signal of the fundamental frequency estimation unit 60 and which is provided for applying a modified pitch processing to at least part of the input audio signals. It is to be understood that in the example of FIG. 1 the CI signal processing block 25 represents the usual or conventional signal processing applied in the sound processor of a CI device, apart from pitch enhancement processing.

The audio signal processing unit 124 of the hearing aid 110 comprises a hearing aid signal processing block 125 for applying the usual or conventional signal processing to the input audio signals and an acoustic pitch enhancement unit 127 which is supplied with the output signal of the fundamental frequency estimation unit 60 and which is provided for applying a modified pitch processing to at least part of the input audio signals.

It has to be understood that according to the present invention modified pitch processing is applied at an appropriate position in the signal processing chain of the neural stimulation signal in the auditory prosthesis device and that in addition a modified pitch processing is also applied in an appropriate position of the signal processing chain of the hearing aid 110, wherein in both cases the modified pitch processing is based on the estimated fundamental frequency of the input audio signal.

The microphones 20, 120 may be implemented physically as part of the CI device 10 and the hearing aid 110, respectively; alternatively or in addition, at least one of the microphones may be a wireless external microphone.

In case that the CI device 10 and the hearing aid 110 are provided for stimulation of different ears, the audio signals captured by the respective microphones 20, 120 may be exchanged via a wireless (or wired) binaural link.

The fundamental frequency estimation unit 60 may use one of the known methods for fundamental frequency estimation, such as an auto-correlation algorithm of the audio signal in the time domain, a pitch tracking algorithm, a spectro-temporal analysis algorithm, a learning algorithm, a neural network algorithm and/or a code-book algorithm.

While in principle it is possible to perform the fundamental frequency estimation in the unit 60 on the basis of the audio signal supplied by a single microphone, performance may be improved by using the audio signals of more than one or even all available microphones in the system. In the example shown in FIG. 1, the fundamental frequency estimation unit 60 uses an input audio signal from each of the microphones 20, 120.

According to one embodiment, the hearing system may comprise a classifier unit 29 which may be provided, for example, as part of the CI device 10, for analyzing the input audio signal in order to provide an output signal representative of the present auditory scene, with the output signal of the classifier unit 29 being supplied to at least one of the electric signal pitch enhancement unit 27 and the acoustic signal pitch enhancement unit 127 in order to adjust at least one parameter used in the modified pitch processing according to the classified auditory scene. Examples of different acoustic situations are speech in quiet surrounding, speech in noisy surrounding, talker with using a tonal language (such as Mandarin Chinese), two or more simultaneous talkers, music, etc. In certain acoustic situations pitch enhancement may be more useful than in other situations; for example, in the absence of speech and music, pitch enhancement is not particularly useful.

Alternatively or in addition, the CI device may be provided with a user interface allowing the CI user to select one of a plurality of different programs specifically designed for a special situation. For example, modified pitch processing in the electric signal pitch enhancement 27 may be applied only in cases where there is a voiced input audio signal (such voiced/unvoiced detector may be implemented in the classifier unit 29). Alternatively, or in addition, the fundamental frequency estimation unit 60 may be disabled in case that there is no voiced input audio signal.

According to a further option, the system, for example the CI device 10, may comprise a control unit 31 which provides an output signal representative of the individual hearing abilities of the patient, with such output signal being supplied to at least one of the electric signal pitch enhancement unit 27 and the acoustic signal pitch enhancement unit 127 in order to adjust at least one parameter used in the modified pitch processing according to the individual hearing abilities of the patient. Thus the individual CI patient's abilities to detect pitch can be taken into account in order to optimize pitch processing. In this respect, results from psychoacoustic pitch perception experiments as well as the residual hearing may serve as a basis for the pitch processing in the acoustic domain; fore example, poor detection thresholds for the spectral contrast require more enhancement, or poor detection threshold for frequency modulation require more increased frequency modulation index. In addition, default pitch processing parameters might be applied or the pitch processing parameters are calculated from the audiogram using standard procedures.

Figure 5:
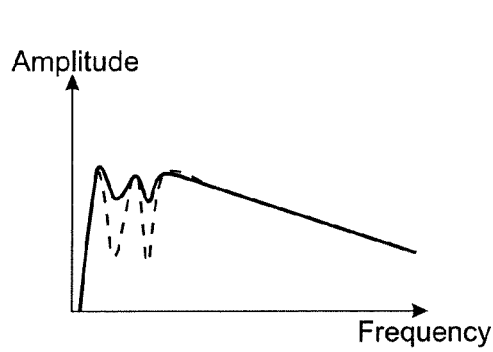
FIG. 5 illustrates an example of pitch enhancement by enhancement of the spectral contrast of the fundamental frequency and its harmonics in the acoustic domain of the system of FIG. 1, with the signal amplitude versus frequency being shown.

The modified pitch processing in the acoustic signal pitch enhancement 127 may include enhancement of the spectral contrast of the fundamental frequency $f_0$ and its harmonics, as illustrated in FIG. 5, wherein the original signal is shown as a solid line and the spectral contrast enhanced signal is shown as a dotted line.

Alternatively or in addition, pitch processing of the acoustic signal may include manipulations in the frequency domain which increase pitch perception, such as an increase of the frequency modulation index and/or shifting of pitch signal components in a frequency range inaudible by a patient into a frequency range audible by the patient.

Such treatment is illustrated in FIG. 6, wherein the fundamental frequency is shown as a function of time, with the fundamental frequency of the original signal being shown as a solid line and with the fundamental frequency of the signal with increased frequency modulation index being shown as a dotted line; the fundamental frequency of the frequency shifted signal is shown as a dashed line (the dashed line actually indicates a signal involving both enhanced frequency modulation index and shifting into an audible range). These options also may be combined.

As already mentioned above, preferably modified pitch processing in the CI device is employed only for voiced input audio signals. According to one option, modified pitch processing may be implemented by using modified temporal queues, i.e. rate or envelope pitch cues. In other words, the unit 27 may apply variations of the stimulation rate in order to enhance pitch perception by the patient. Alternatively or in addition the unit 27 may apply variations of the stimulation pattern in order to enhance pitch perception. For example, sinusoidal amplitude modulation may be applied to the slowly varying envelope signals, with the frequency of the sinusoidal modulation corresponding to the fundamental frequency of the input audio signal. Such type of processing enhances pitch perception by means of envelope pitch. Alternative, as already mentioned above, a stimulation rate modulated pulse train may be employed. In such modified temporal processing inherent envelope fluctuations may be minimized by applying a low pass filter to the input audio signal.

According to the most simple approach, the modified pitch processing, i.e. the modulator signal, may be applied to each spectral channel of the CI device 10.

According to a preferred more elaborated approach, the modified pitch processing is applied only to channels whose SNR is above a predetermined limit, such as 0 dB, with the processing of the remaining channels not being altered. Thereby the effect of modulation masking in the detection of speech component may be minimized. It is expected that this type of processing is more efficient for speech in noise situations.

Rather than applying modified pitch processing only to such speech dominated channels (channels whose SNR is greater than 0 dB), modified pitch processing may be applied only to noise dominated channels (i.e. channels whose SNR is smaller than 0 dB).

Such processing is illustrated by example shown in FIG. 7, wherein only the channel A at the top and the channel D at the bottom are selected for modified pitch processing.

Typically, a CI device uses an electrode array for electric stimulation of the auditory nerve in the cochlea. However, the CI device alternatively or in addition may employ optically and/or thermal stimulation of the auditory nerve in the cochlea.

While the present invention so far has been illustrated by reference to an example using a CI device as the auditory prosthesis device applying a neural stimulation signal to the patient, the invention also may be used for other auditory prosthesis devices, such as an auditory brain stem implant or an auditory midbrain implant.

Figure 2:
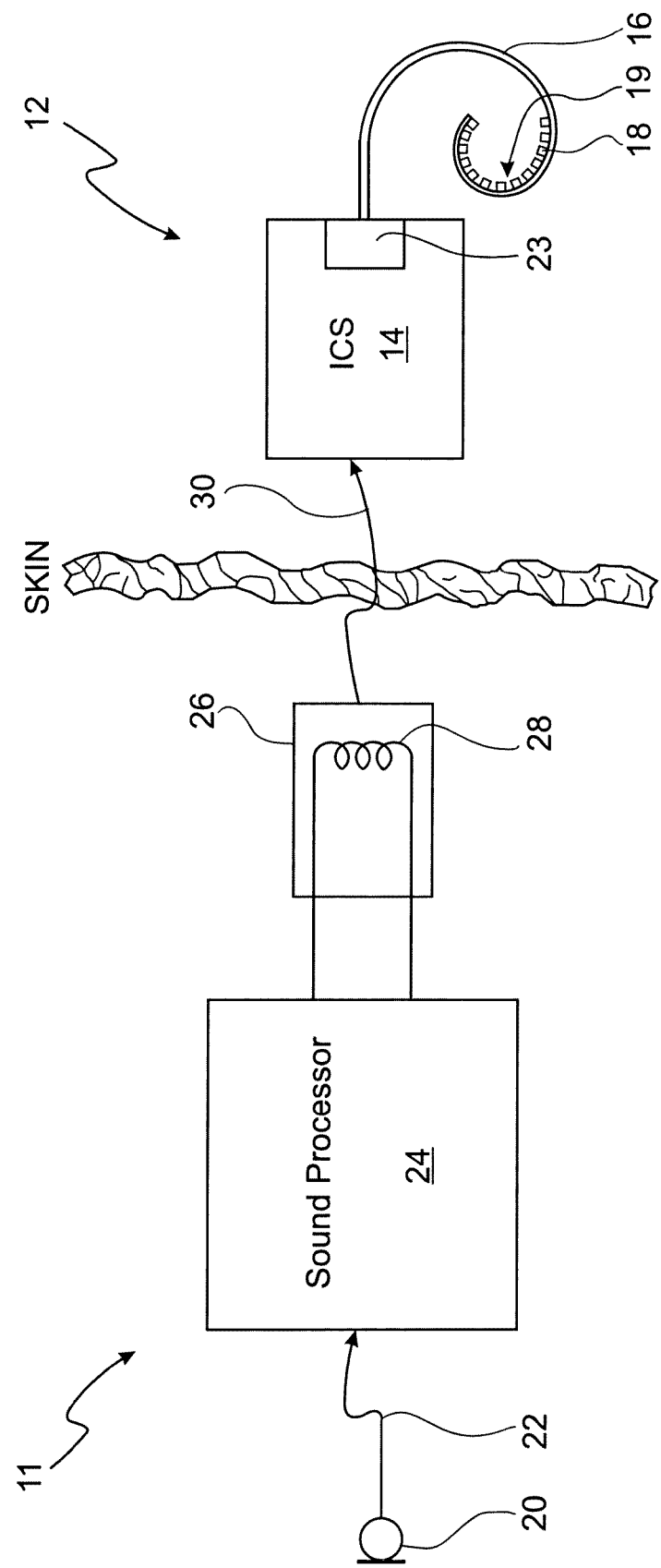
FIG. 2 is a schematic view of an example of a CI device to be used in the hearing system of FIG. 1.
Figure 3:
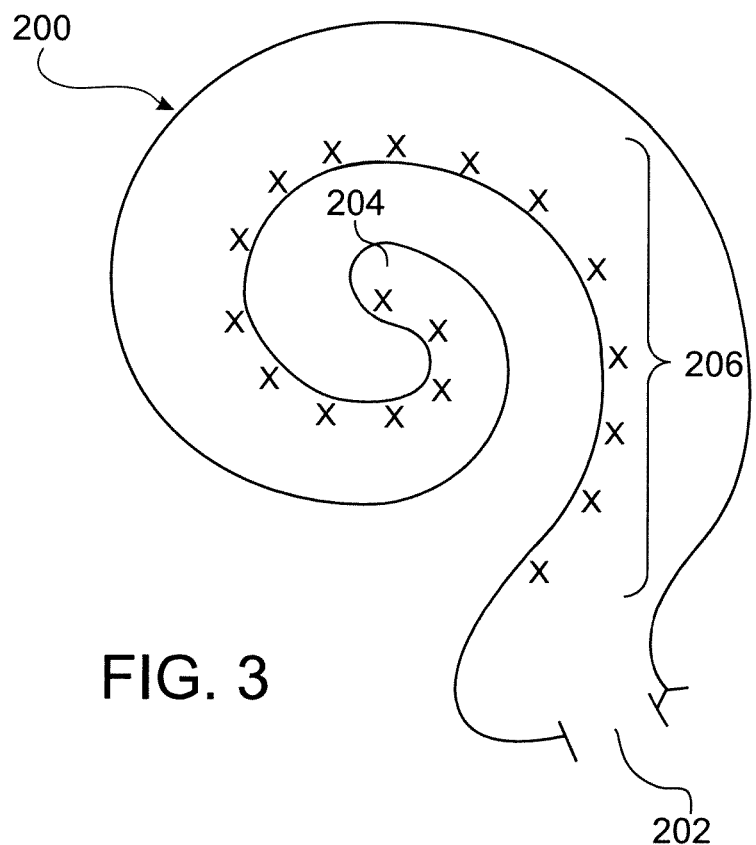
FIG. 3 is a schematic cross-sectional view of a human cochlea with marked stimulation sites.
Figure 4:
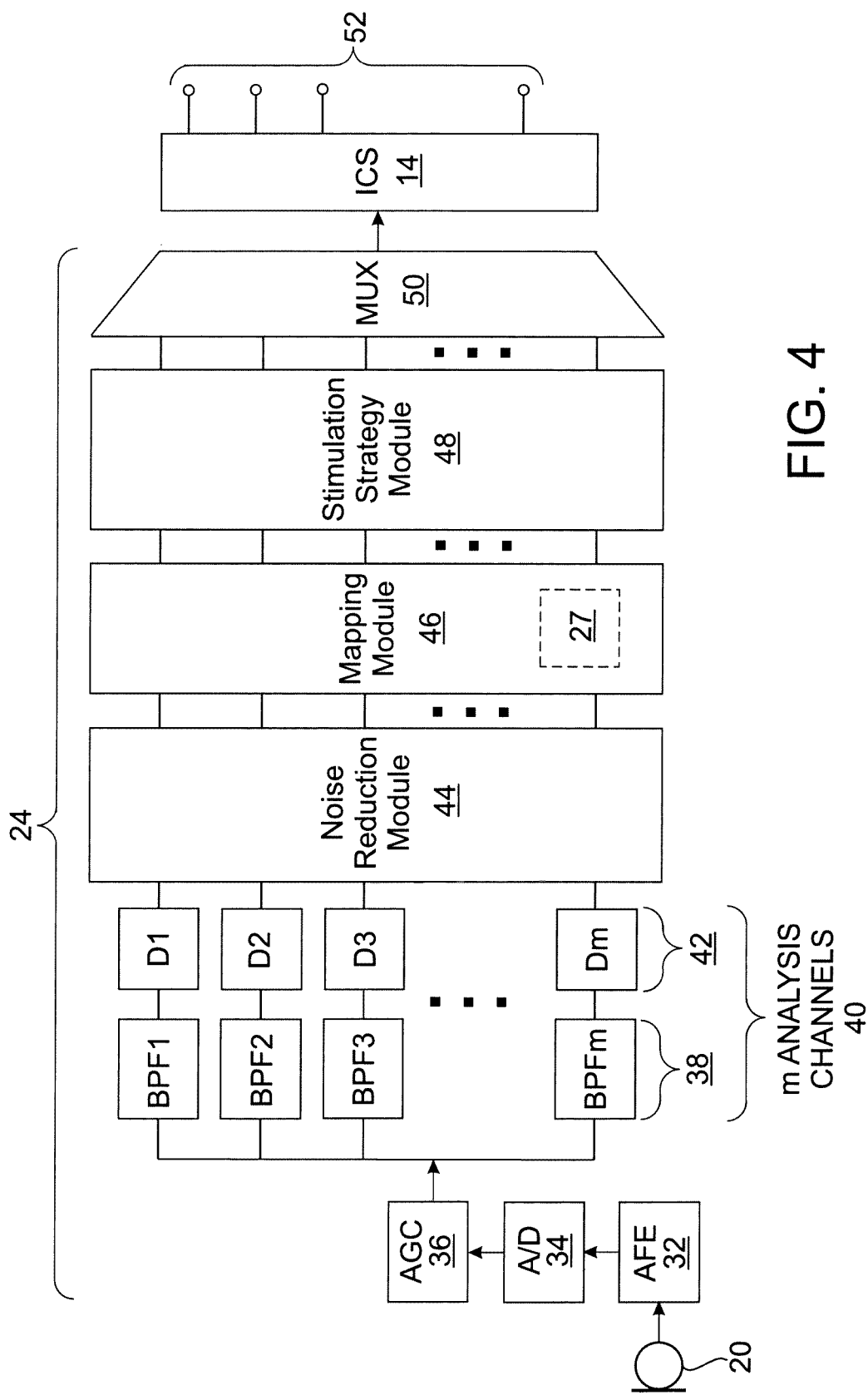
FIG. 4 is a block diagram of the signal processing structure of the CI device of FIG. 2.

An example of a CI device 10 to be used with the invention is illustrated in more detail in FIGS. 2 to 4. The device comprises a sound processing sub-system 11 and a stimulation sub-system 12. The sound processing sub-system 11 serves to detect or sense an audio signal and divide the audio signal into a plurality of analysis channels each containing a frequency domain signal (or simply "signal") representative of a distinct frequency portion of the audio signal. A signal level value and a noise level value are determined for each analysis channel by analyzing the respective frequency domain signal, and a noise reduction gain parameter is determined for each analysis channel as a function of the signal level value and the noise level value of the respective analysis channel. Noise reduction is applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to as "stimulation current" and/or "stimulation pulses") to stimulation sites at the auditory nerve within the cochlear of a patient in accordance with the stimulation parameters received from the sound processing sub-system 11. Electrical stimulation is provided to the patient via a CI stimulation assembly 18 comprising a plurality of stimulation channels, wherein various known stimulation strategies, such as current steering stimulation and/or N-of-M stimulation, may be utilized (a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes).

An "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

FIG. 3 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 2, the stimulation subsystem 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient; however, in alternative examples, at least one of the components of the sub-system 11 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30.

The link 30 may include a bidirectional communication link and/or one or more dedicated unidirectional communication links. According to an alternative embodiment, the sound processor 24 and the ICS 14 may be directly connected by wires.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a plurality of filters 38 (for example, bandpass filters) which are configured to divide the digital signal into analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 are input into a noise reduction module 44, wherein the signals are treated in a manner so as to reduce noise in the signal in order to enhance, for example, the intelligibility of speech by the patient. Examples of the noise reduction module 44 are described e.g. in WO 2011/032021 A1.

The noise reduced signals are supplied to a mapping module 46 which serves to map the signals in the analysis channels 40 to the stimulation channels. For example, signal levels of the noise reduced signals may be mapped to amplitude values used to define the electrical stimulation pulses that are applied to the patient by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality of the stimulation channels 52 in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 operates in accordance with at least one control parameter. Such control parameters may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values and/or filter characteristics. Examples of such auditory prosthesis devices, as described so far, can be found, for example, in WO 2011/032021 A1.

The electric signal pitch enhancement unit 27 shown in FIG. 1 may be implemented, for example, as part of the mapping module 46.

The invention claimed is:

1. A hearing assistance system comprising an auditory prosthesis device for neural stimulation of a patient's hearing at one of the patient's ears and a hearing aid for acoustic stimulation of the patient's hearing at the same one or the other one of the patient's ears, the system including:
   at least one microphone for capturing an input audio signal from ambient sound; and
   a fundamental frequency estimation unit for estimating the fundamental frequency and at least part of its harmonics at least for voiced segments of the input audio signal and for supplying a corresponding output signal;
   the auditory prosthesis comprising:
      a sound processor for generating a neural stimulation signal from at least part of the input audio signal, the sound processor comprising an electric signal pitch enhancement unit supplied with the output signal of the fundamental frequency estimation unit, the electric signal pitch enhancement unit being provided for applying a modified pitch processing when generating the neural stimulation signal, and
      an implantable stimulation assembly for stimulation of the patient's hearing according to the neural stimulation signal;
   the hearing aid comprising:
      an audio signal processing unit for processing at least part of the input audio signal, the audio signal processing unit comprising an acoustic signal pitch enhancement unit supplied with the output signal of the fundamental frequency estimation unit,
      the acoustic signal pitch enhancement unit being provided for applying a modified pitch processing in the audio signal processing, and
      an acoustic output transducer for stimulating the patient's hearing according to the processed audio signals.

2. The system of claim 1, further comprising a plurality of microphones, wherein the fundamental frequency estimation unit is adapted to use an input audio signal from each of the microphones.

3. The system of claim 2, wherein both the auditory prosthesis device and the hearing aid are provided with at least one of the microphones.

4. The system of claim 3, wherein the auditory prosthesis device and the hearing aid are for stimulation of different ones of the patient's ears, and wherein the audio signal of the microphones of the auditory prosthesis device and the hearing aid are exchanged via a wireless or a wired link.

5. The system of claim 2, wherein at least one of the microphones is a wireless external microphone.

6. The system of claim 1, wherein the fundamental frequency estimation unit is provided as part of the auditory prosthesis device.

7. The system of claim 1, wherein the fundamental frequency estimation unit is provided as part of the hearing aid.

8. The system of claim 1, wherein the fundamental frequency estimation unit is adapted to use at least one of an auto-correlation algorithm of the audio signal in the time domain, a pitch tracking algorithm, a spectro-temporal analysis algorithm, a learning algorithm, a neural network algorithm, and a code-book algorithm.

9. The system of claim 1, further comprising a classifier unit for analyzing the input audio signal in order to provide an output signal representative of the present auditory scene, and wherein the output signal of the classifier unit is supplied to at least one of the electric signal pitch enhancement unit and the acoustic signal pitch enhancement unit in order to adjust at least one parameter used in the electric signal pitch enhancement unit and the acoustic signal pitch enhancement unit, respectively, according to the classified auditory scene.

10. The system of claim 1, further comprising a control unit for provide an output signal representative of the individual hearing abilities of the patient, and wherein the output signal of the control unit is supplied to at least one of the electric signal pitch enhancement unit and the acoustic signal pitch enhancement unit in order to adjust at least one parameter used in the electric signal pitch enhancement unit and the acoustic signal pitch enhancement unit, respectively, according to the individual hearing abilities of the patient.

11. The system of claim 1, wherein the acoustic signal pitch enhancement unit is adapted to enhance the spectral contrast of the fundamental frequency and its harmonics.

12. The system of claim 1, wherein the acoustic signal pitch enhancement unit is adapted to increase a frequency modulation index.

13. The system of claim 1, wherein the acoustic signal pitch enhancement unit is adapted to shift signal components in a frequency range inaudible by the patient into a frequency range audible by the patient.

14. The system of claim 1, further comprising a voiced/unvoiced detector for detecting voiced segments of the input audio signal, wherein the electric signal pitch enhancement unit is adapted to apply a modified pitch processing only to voiced segments of the input audio signal.

15. The system of claim 1, wherein the electric signal pitch enhancement unit is adapted to apply variations of a stimulation rate to enhance pitch.

16. The system of claim 15, wherein the electric signal pitch enhancement unit is adapted to employ a stimulation rate modulated pulse train.

17. The system of claim 1, wherein the electric signal pitch enhancement unit is adapted to apply variations of a stimulation pattern to enhance pitch.

18. The system of claim 17, wherein the electric signal pitch enhancement unit is adapted to apply sinusoidal amplitude modulation to envelope signals.

19. The system of claim 18, wherein the frequency of the sinusoidal amplitude modulation corresponds to the fundamental frequency of the input audio signal.

20. The system of claim 1, wherein the electric signal pitch enhancement unit is adapted to minimize envelope fluctuations by applying a low-pass filter to the input audio signal.

21. The system of claim 1, wherein the sound processor is provided with a filterbank for dividing the input audio signal into a plurality of analysis channels, each containing a frequency domain signal representative of a distinct frequency portion of the audio signal.

22. The system of claim 21, wherein the electric signal pitch enhancement unit is adapted to act only on those channels whose signal-to-noise ratio is above a pre-determined limit.

23. The system of claim 21, wherein the electric signal pitch enhancement unit is adapted to act only on those channels whose signal-to-noise ratio is below a pre-determined limit.

24. The system of claim 1, wherein the auditory prosthesis device comprises a cochlear implant arrangement, and wherein the neural stimulation signal is an auditory nerve stimulation signal.

25. The system of claim 1, wherein the auditory prosthesis device comprises at least one of an auditory brainstem implant and an auditory midbrain implant.

26. A method of combined acoustic and neural stimulation of a patient's hearing, comprising:
capturing an input audio signal from ambient sound via at least one microphone;
estimating the fundamental frequency and at least part of its harmonics at least for voiced segments of the input audio signal;
generating, by a sound processor, a neural stimulation signal from the input audio signal, wherein a modified pitch processing according to the estimated fundamental frequency being applied in said generating of a neural stimulation signal, and stimulating, by an implantable stimulation assembly, the patient's hearing according to the neural stimulation signal;
generating an acoustic stimulation signal by processing at least part of the input audio signal, with a modified pitch processing according to the estimated fundamental frequency being applied in said processing, and stimulating the patient's hearing according to the processed audio signals via an acoustic output transducer.

* * * * *